United States Patent
Corradi et al.

(10) Patent No.: US 9,328,040 B2
(45) Date of Patent: May 3, 2016

(54) PROCESS FOR RECOVERING BENZENE AND FUEL GAS IN AN AROMATICS COMPLEX

(71) Applicant: UOP LLC, Des Plaines, IL (US)

(72) Inventors: Jason T. Corradi, Arlington Heights, IL (US); Ian G. Horn, Steamwood, IL (US); Gregory R. Werba, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 305 days.

(21) Appl. No.: 14/195,000

(22) Filed: Mar. 3, 2014

(65) Prior Publication Data

US 2015/0246858 A1 Sep. 3, 2015

(51) Int. Cl.
*C07C 7/04* (2006.01)
*C07C 7/00* (2006.01)

(52) U.S. Cl.
CPC .. *C07C 7/005* (2013.01); *C07C 7/04* (2013.01)

(58) Field of Classification Search
None
See application file for complete search history.

(56) References Cited

U.S. PATENT DOCUMENTS

| | | | | |
|---|---|---|---|---|
| 2,968,631 A | * | 1/1961 | Brozowski | B01J 23/94 502/50 |
| 4,118,429 A | * | 10/1978 | Fritsch | C07C 5/2702 208/143 |
| 4,203,826 A | * | 5/1980 | Mayes | C10G 35/04 208/134 |
| 4,783,568 A | * | 11/1988 | Schmidt | C07C 15/08 585/475 |
| 6,004,452 A | | 12/1999 | Ash et al. | |
| 6,740,788 B1 | | 5/2004 | Maher et al. | |
| 6,958,425 B1 | | 10/2005 | Bogdan et al. | |
| 7,169,368 B1 | | 1/2007 | Sullivan et al. | |
| 8,431,758 B2 | | 4/2013 | Frey et al. | |
| 8,609,922 B2 | | 12/2013 | Werba et al. | |
| 2003/0092952 A1 | * | 5/2003 | Netzer | C10G 69/12 585/648 |
| 2012/0048711 A1 | | 3/2012 | Werba et al. | |
| 2013/0233698 A1 | | 9/2013 | Corradi et al. | |
| 2015/0376086 A1 | * | 12/2015 | Tinger | B01J 19/2445 585/314 |

FOREIGN PATENT DOCUMENTS

CN 103242130 A 8/2013

* cited by examiner

*Primary Examiner* — Tam M Nguyen

(57) ABSTRACT

A process for separating xylene from a feedstock in which the feedstock is separated into a xylene stream, a benzene rich stream and a light ends stream. Two separation zones may be utilized in which liquid from both is sent to a stabilization zone and the vapor from the stabilization zone is combined with a stream prior to the stream entering the second separation zone.

20 Claims, 1 Drawing Sheet

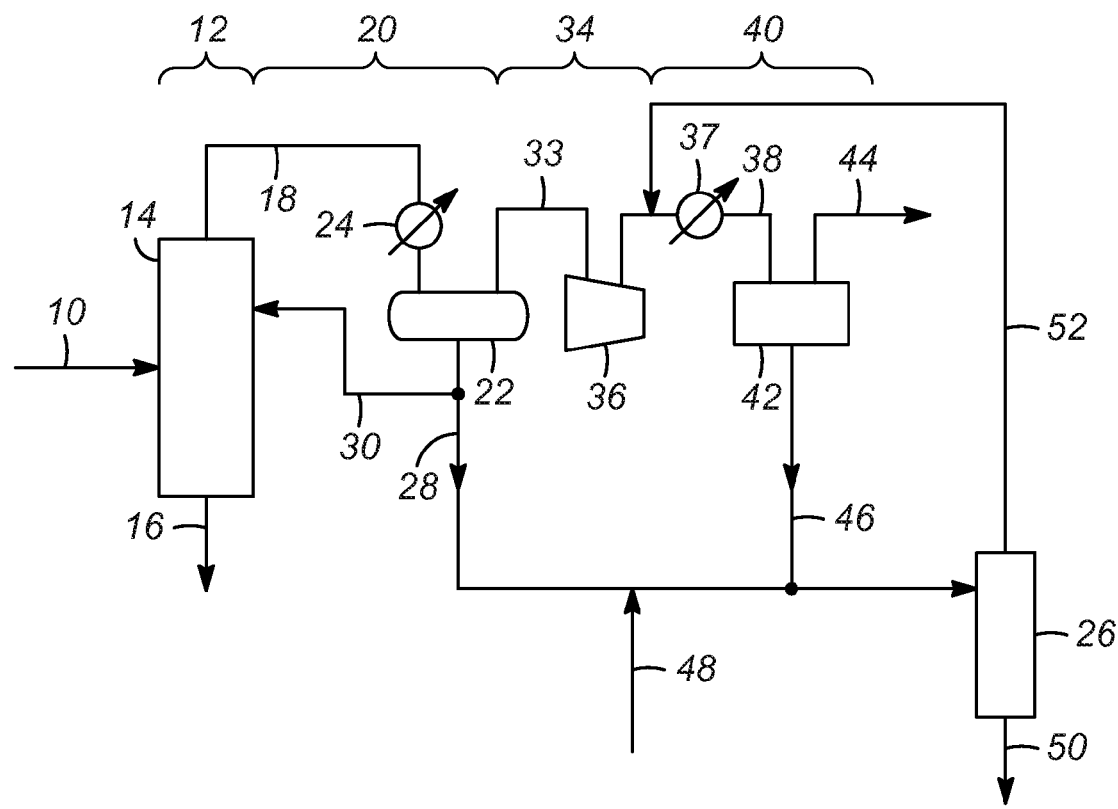

US 9,328,040 B2

PROCESS FOR RECOVERING BENZENE AND FUEL GAS IN AN AROMATICS COMPLEX

FIELD OF THE INVENTION

This invention relates to an improved process for energy savings in the distillation of hydrocarbons. More specifically, the present invention concerns energy conservation within an aromatics-processing complex producing xylene isomers, benzene and fuel gas.

BACKGROUND OF THE INVENTION

The xylene isomers are produced in large volumes from petroleum as feedstocks for a variety of important industrial chemicals. The most important of the xylene isomers is para-xylene, the principal feedstock for polyester, which continues to enjoy a high growth rate from large base demand. Ortho-xylene is used to produce phthalic anhydride, which supplies high-volume but relatively mature markets. Meta-xylene is used in lesser, but growing, volumes for products such as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha, but not in sufficient volume to meet demand; thus, conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

Aromatics complexes producing xylenes are substantial consumers of energy, notably in distillation operations to prepare feedstocks and separate products from conversion processes. The separation of xylenes from a feedstock in particular offers substantial potential for energy savings. Energy conservation in such processes would not only reduce processing costs, but also address current concerns about carbon emissions.

In addition to producing xylenes, valuable fuel gas is generated during the catalytic conversion of xylenes in an aromatics complex. A portion of this fuel gas is recoverable in a xylene isomerization unit.

The xylene isomerization units typically include a deheptanizer and a stabilizer. The current designs for xylene isomerization units utilize at least two recycle loops between the deheptanizer and the stabilizer.

In the first recycle loop, at least a portion of the overhead vapor from the stabilizer is recycled back to the deheptanizer. This will result in this portion of the vapor being re-condensed, re-flashed, and ultimately re-compressed in the same separation process since it is passed back to the deheptanizer and will pass through the same separation equipment.

The second recycle loop is formed between a receiver and a vent drum where the chilled liquid from the vent drum enters the hotter, low pressure receiver and re-flashes into vapor to the compressor. This requires the same compounds to be re-compressed and cooled once again.

It is believed that the current design is inefficient at least because both of the recycle loops lead to undesirable re-processing of the same material at the expense of equipment capacity and utility cost. Energy conservation in such processes would not only reduce processing costs but also would address current concerns about carbon emissions.

Therefore, there is a need to provide a xylene isomerization process which may be carried out more efficiently.

SUMMARY OF THE INVENTION

Accordingly, in an embodiment of the present invention, a method for recovering benzene and fuel gas in a xylene isomerization process is provided in which a feedstock is passed into a deheptanizer zone in which the feedstock is separated into a deheptanizer vapor phase and a deheptanizer liquid phase, the deheptanizer vapor phase containing hydrocarbons with seven carbon atoms or less, and the deheptanizer liquid phase containing mostly hydrocarbons with eight carbon atoms or more; the deheptanizer vapor phase is passed from the deheptanizer zone to a first separation zone; the deheptanizer vapor phase is separated in the first separation zone into a first liquid phase and a first vapor phase; the first liquid phase is passed from the first separation zone to a stabilization zone; the first vapor phase is passed from the first separation zone to a compression zone in which the first vapor phase is compressed to provide a compressed vapor phase; the compressed vapor phase is passed from the compression zone to a second separation zone; the compressed vapor phase is cooled to form a second liquid phase and a second vapor phase, the second vapor phase being a light ends vapor stream; the light ends vapor stream is recovered; the second liquid phase is passed to the stabilization zone; the first liquid phase and the second liquid phase are separated in the stabilization zone into a recycle vapor phase and a benzene rich liquid stream; the benzene rich liquid stream is recovered; and, the recycle vapor phase is passed to the second separation zone, wherein the recycle vapor phase is cooled prior to entering the second separation zone.

In other embodiments of the present invention, a method for recovering benzene and fuel gas in a xylene isomerization process is provided in which a feedstock is passed into a distillation zone in which the feedstock is separated into a distillation vapor and a distillation liquid, the distillation vapor containing hydrocarbons with seven carbon atoms or less; the distillation vapor is condensed; the distillation vapor is separated into a first liquid phase and a first vapor phase; the first liquid phase is passed to a stabilization zone; the first vapor phase is compressed into a compressed vapor phase; the compressed vapor phase is cooled to form a second liquid phase and a second vapor phase, the second vapor phase being a light ends vapor stream; the light ends vapor stream is recovered as fuel gas; the second liquid phase is passed to the stabilization zone; the first liquid phase and the second liquid phase are separated in the stabilization zone into a recycle vapor stream and a benzene rich liquid stream; the benzene rich liquid stream is recovered; and, the recycle vapor stream is combined with the compressed vapor phase to create a recycle loop.

In even further embodiments of the present invention a method of recovering benzene and fuel gas in a xylene isomerization process is provided in which, a feedstock is passed into a separation zone in which the feedstock is separated into a vapor stream and a liquid stream, the vapor stream containing hydrocarbons with seven carbon atoms or less, the liquid stream comprising xylene; the vapor stream from the separation zone is condensed; the vapor stream is separated into a first liquid phase and a first vapor phase; the first liquid phase is passed to a stabilization zone; the first vapor phase is compressed into a compressed vapor phase; the compressed vapor phase is cooled and separated into a second liquid phase and a second vapor phase, the second vapor phase being a light ends vapor stream; the light ends vapor stream is recovered as fuel gas; the second liquid phase is passed to the stabilization zone; the first liquid phase and the second liquid phase is separated in the stabilization zone into a recycle vapor stream and a benzene rich liquid stream; and, the benzene rich liquid stream is recovered.

It is believed that one or more of the embodiments of the present invention described herein are beneficial and desirable for a number of reasons.

DETAILED DESCRIPTION OF THE DRAWING

The drawing is simplified process flow diagram in which the FIGURE shows a xylene isomerate recovery process according to one or more embodiments of the present invention.

DETAILED DESCRIPTION OF THE INVENTION

A process has been developed for separating xylene from a feedstock. The feedstock to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feedstock to the process of the invention may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. If the feedstock is catalytic reformate, the reformer preferably is operated at high severity to achieve high aromatics yield with a low concentration of nonaromatics in the product.

The FIGURE shows a simplified flow diagram of an xylene isomerate recovery portion of an aromatics-processing complex for a feedstock which typically contains olefinic compounds and light ends, e.g., butanes and lighter hydrocarbons and such as pentanes, as well as benzene, toluene and $C_8$ aromatics and higher aromatics and aliphatic hydrocarbons including naphthenes.

The feedstock is introduced via a line 10 to a xylene separation zone 12. The xylene separation zone 12 includes a column 14. Preferably the column 14 is a distillation column, and most preferably a deheptanizer As will be appreciated by one of ordinary skill in the art, such a column 14 may contain trays or mechanical packing.

In the xylene separation zone 12, the feedstock is separated into a vapor phase and a liquid phase. The liquid phase contains most of the xylene as well as other heavier hydrocarbons. The liquid phase may be recovered from the xylene separation zone 12 via a line 16 and passed to further processing units to recover the desired xylene isomer and other valuable byproducts. The further processing units are known to those of ordinary skill in the art and are not necessary for a full understanding of the present invention.

The vapor phase in the xylene separation zone 12 contains hydrocarbons with seven carbon atoms or less, benzene, and toluene. As will be appreciated by those of ordinary skill in the art, when separating hydrocarbons, there are equilibrium distributions of components in vapor and liquid streams in close contact during the separation processes and thus, the present invention is intended to accommodate a range of aromatic and non-aromatic component purities.

The vapor phase is recovered from the xylene separation zone 12 and passed via a line 18 to a first separation zone 20. However, prior to reaching the first separation zone 20, the vapor phase is condensed. Accordingly, a condenser 24 is provided in the line 18 used to pass the vapor phase from the xylene separation zone 12 to the first separation zone 20.

The first separation zone 20 typically includes a vessel 22. Preferably the vessel 22 of the first separation zone 20 has a temperature between approximately 32° C. to 149° C. In the vessel 22, the vapor phase from the xylene separation zone 12 is separated into a first liquid phase and a first vapor phase. The first liquid phase comprises benzene and toluene as well as soluble levels of hydrocarbons with five carbons or less dissolved into the liquid phase. The first vapor phase comprises mostly hydrogen, and hydrocarbons with four carbons or less. Again, there will be some crossover amounts of compounds. The first liquid phase from the first separation zone 20 may be passed to a stabilization zone 26 (discussed below) via a line 28. Additionally, a portion of the first liquid phase from the first separation zone 20 may be recycled to the xylene separation zone 12 via a line 30.

The first vapor phase from the first separation zone 20 is passed via a line 33 to a compression zone 34 in which the first vapor phase is compressed into a compressed vapor phase. The compression zone 34 includes at least a compressor 36. Preferably, the first vapor phase is cooled in the compression zone 34 as well, Accordingly, the compression zone 34 may also include a condenser 37.

From the compression zone 34, the compressed vapor phase is passed via a line 38 to a second separation zone 40 which typically includes a vessel 42 typically having an inlet distributor to facilitate the separation of the compressed vapor phase, and which may also have a drop leg for decanting a heavy aqueous liquid phase that can be formed if water is present in the column feed. The temperature of the second separating zone 40 is typically between approximately 10° C. to 149° C. In the second separation zone 40, the compressed vapor phase is separated into a second liquid phase and a second vapor phase.

The second vapor phase comprises a light ends vapor stream which includes hydrocarbons having four carbon atoms or less and hydrogen. The light ends vapor stream may be recovered from the second separation zone 40 via a line 44, and, for example, may be passed back to a reaction zone (not shown), may be used as fuel, or be used for other processes.

In prior art systems, the second liquid phase from the vessel 42 in the second separation zone 40 would have been passed to the vessel 22 in the first separation zone 20, which would result in the second liquid phase, which is cool, being introduced into the vessel 22, which is hot. Accordingly, compounds which were previously condensed into liquid will be evaporated into vapor essentially wasting the energy supplied into the system to condense the compounds originally. Further, additional energy will now be required to re-compress and re-condense the same compounds.

The present invention avoids wasting this energy by instead passing the second liquid phase from the second separation zone 40 to the stabilizing zone 26 via a line 46.

In the stabilization zone 26, the first liquid phase from the first separation zone 20 and the second liquid phase from the second separation zone 40 are separated into a recycle vapor phase and a benzene rich liquid stream. The two liquid phases may also be combined with another benzene rich stream from, for example, an aromatic transalkylation unit via a line 48.

The benzene rich liquid stream comprises non-aromatics, toluene, and benzene. The benzene rich liquid stream may be further recovered via a line 50 and processed to separate out the benzene and other valuable aromatics, or it may be stored and then processed further (not shown).

In the known processes, the recycle vapor phase from the stabilization zone 26 is typically returned to the xylene separation zone 12. However, such a process will unnecessarily consume additional energy by re-compressing the compounds of the recycle vapor phase which have already been separated out from the feedstock.

In the present invention, the recycle vapor phase is passed to the second separation zone 40 via a line 52. Preferably, the recycle vapor phase is combined with the compressed vapor phase being passed into the second separation zone 40 in the line 38.

Most preferably, this occurs prior to the compressed vapor phase passing through the condenser 37 in the line 38. Since the amount of vapor that is recycling back through compression zone 34 is smaller, this will allow for a smaller compressor and related equipment to be utilized, which, in turn, will result in greater savings on both capital expenditures and operating expenses.

Based on a theoretical modeling of a paraxylene aromatics complex producing 1000 KMTA and utilizing one or more embodiments of the present invention, the vent gas compressor size may be reduced by up to 10% and the power consumption of same is reduced by 25% compared to a typical paraxylene aromatics complex. Additionally, overall annual utility savings are expected to be approximately $100,000 using typical utility pricing as a result of these reductions. Additional utility and operating costs savings could be realized, for example, by optimizing the stabilizer feed temperature.

As will be appreciated, a process according to one or more of these embodiments provides an effective and efficient method to separate xylene from a reaction effluent.

More specifically, in one or more embodiments of the present invention, unnecessary re-compression of overhead vapor from the stabilization zone 26 is eliminated.

Additionally, in one or more embodiments of the present invention, the unnecessary re-flashing, re-compression, and re-cooling of the second liquid phase from the second separation zone 40 has been eliminated, While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for the recovery of a benzene rich liquid stream and a light ends vapor stream in a xylene isomerization process from a feedstock, the method comprising:
    passing a feedstock into a deheptanizer in which the feedstock is separated into a deheptanizer vapor phase and a deheptanizer liquid phase, the deheptanizer vapor phase containing hydrocarbons with seven carbon atoms or less, and the deheptanizer liquid phase containing hydrocarbons with eight carbon atoms or more;
    passing the deheptanizer vapor phase from the deheptanizer to a first separation zone;
    separating the deheptanizer vapor phase in the first separation zone into a first liquid phase and a first vapor phase;
    passing the first liquid phase from the first separation zone to a stabilization zone;
    passing the first vapor phase from the first separation zone to a compression zone in which the first vapor phase is compressed to provide a compressed vapor phase;
    passing the compressed vapor phase from the compression zone to a second separation zone;
    separating the compressed vapor phase into a second liquid phase and a second vapor phase in the second separation zone, the second vapor phase being a light ends vapor stream;
    recovering the light ends vapor stream;
    passing the second liquid phase to the stabilization zone;
    separating the first liquid phase and the second liquid phase in the stabilization zone into a recycle vapor phase and a benzene rich liquid stream;
    recovering the benzene rich liquid stream; and,
    passing the recycle vapor phase to the second separation zone, wherein the recycle vapor phase is cooled prior to entering the second separation zone.

2. The method of claim 1 further comprising:
    passing a portion of the first liquid phase to the deheptanizer.

3. The method of claim 1 further comprising:
    passing a benzene rich stream from an aromatic transalkylation unit to the stabilization zone.

4. The method of claim 1 further comprising:
    passing the benzene rich liquid stream to an extraction zone to recover a benzene stream.

5. The method of claim 1 further comprising:
    passing the benzene rich liquid stream to storage.

6. The method of claim 1 further comprising:
    compressing the deheptanizer vapor stream before the deheptanizer vapor stream enters the first separation zone.

7. The method of claim 6 wherein a temperature of the first separation zone is between approximately 32° C. to 149° C.

8. The method of claim 7 wherein a temperature of the second separation zone is between approximately 10° C. to 149° C.

9. The method of claim 1 wherein a temperature of the first separation zone is between approximately 10° C. to 149° C. and a temperature of the second separation zone is between approximately 10° C. to 149° C.

10. A method tier the recovery of a benzene rich liquid stream and a light ends vapor stream in a xylene isomerization process from a feedstock, the method comprising:
    passing a feedstock into a distillation column in which the feedstock is separated into a distillation vapor and a distillation liquid, the distillation vapor containing mostly hydrocarbons with seven carbon atoms or less;

condensing the distillation vapor;

separating the distillation vapor into a first liquid phase and a first vapor phase;

passing the first liquid phase to a stabilization zone;

compressing the first vapor phase into a compressed vapor phase;

separating the compressed vapor phase into a second liquid phase and a second vapor phase, the second vapor phase being a light ends vapor stream;

recovering the light ends vapor stream;

passing the second liquid phase to the stabilization zone;

separating the first liquid phase and the second liquid phase in the stabilization zone into a recycle vapor stream and a benzene rich liquid stream;

recovering the benzene rich liquid stream; and, combining the recycle vapor stream with the compressed vapor phase.

11. The method of claim 10 wherein a temperature of the first liquid phase is between approximately 32° C. to 149° C.

12. The method of claim 11 wherein a temperature of the compressed vapor phase is between approximately 10° C. to 149° C.

13. The method of claim 10 further comprising:
passing a portion of the first liquid phase to the distillation column.

14. The method of claim 10 further comprising:
passing a benzene rich stream from an aromatic transalkylation unit to the stabilization zone.

15. The method of claim 10 further comprising:
passing the benzene rich liquid stream to an extraction zone to recover a benzene stream.

16. The method of claim 10 further comprising:
passing the benzene rich liquid stream to storage.

17. A method for the recovery of a benzene rich liquid stream and a light ends vapor stream in a xylene isomerization process from a feedstock, the method comprising:

passing a feedstock into a separation zone in which the feedstock is separated into a vapor stream and a liquid stream, the vapor stream containing mostly hydrocarbons with seven carbon atoms or less, the liquid stream comprising xylene;

condensing the vapor stream;

separating the vapor stream into a first liquid phase and a first vapor phase;

passing the first liquid phase to a stabilization zone;

compressing the first vapor phase into a compressed vapor phase;

separating the compressed vapor phase into a second liquid phase and a second vapor phase, the second vapor phase being a light ends vapor stream;

recovering the light ends vapor stream;

passing the second liquid phase to the stabilization zone;

separating the first liquid phase and the second liquid phase in the stabilization zone into a recycle vapor stream and a benzene rich liquid stream; and, recovering the benzene rich liquid stream.

18. The method of claim 17 wherein a temperature of the first liquid phase is between approximately 32° C. to 149° C.

19. The method of claim 18 further comprising:
combining the recycle vapor stream with the compressed vapor phase to create a recycle loop.

20. The method of claim 11 wherein a temperature of the compressed vapor phase is between approximately 10° C. to 149° C.

* * * * *